United States Patent [19] [11] 4,402,947
Moeschler et al. [45] Sep. 6, 1983

[54] PESTICIDALLY ACTIVE NIKKOMICIN HEAVY METAL SALTS

[75] Inventors: Heinrich F. Moeschler, Cologne; Klaus Sasse, Bergisch-Gladbach; Peter M. Lange, Leverkusen; Christian Gölker, Wuppertal; Gerhard Zoebelein, Leverkusen; Otto Telle, Cologne, all of Fed. Rep. of Germany

[73] Assignee: Bayer Aktiengesellschaft, Leverkusen, Fed. Rep. of Germany

[21] Appl. No.: 308,725

[22] Filed: Oct. 5, 1981

[30] Foreign Application Priority Data

Oct. 25, 1980 [DE] Fed. Rep. of Germany ....... 3040293

[51] Int. Cl.$^3$ ...................... A61K 31/71; C07H 19/16; C07H 19/18

[52] U.S. Cl. ..................................... 424/181; 424/180; 536/24

[58] Field of Search ................... 536/24; 424/181, 180

[56] References Cited

U.S. PATENT DOCUMENTS 4,046,881  9/1977  Dähn et al. .......................... 424/181
4,158,608  6/1979  Dähn et al. .......................... 195/80 R
4,287,186  9/1981  Zähner et al. ........................ 536/24

Primary Examiner—Nicky Chan
Attorney, Agent, or Firm—Sprung, Horn, Kramer & Woods

[57] ABSTRACT

Arthropodicidally and fungicidally active heavy metal salts of nikkomicin are produced by reacting nikkomicin with a water-soluble heavy metal salt in an aqueous medium.

5 Claims, No Drawings

PESTICIDALLY ACTIVE NIKKOMICIN HEAVY METAL SALTS

The present invention relates to certain new nikkomicin salts, to a process for their production and to their use as pesticides.

Nikkomicin, its preparation by a microbiological route by means of the strain *Streptomyces tendae* Ettlingen (CBS 354.75) and its use as a plant protection agent are known (see German Offenlegungsschrift (German Published Specification) No. 2,537,028 and U.S. Pat. Nos. 4,046,881 and 4,158,608). It has been found that the nikkomicin obtained in this manner consists of a mixture of similar substances which are called nikkomicins. The main constituents of the nikkomicin mixtures obtained during the fermentation and working up correspond to the general formula

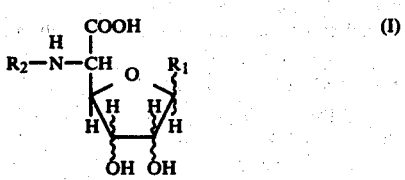

in which
R¹ denotes

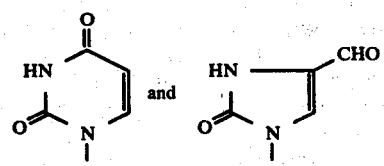

and
R² denotes

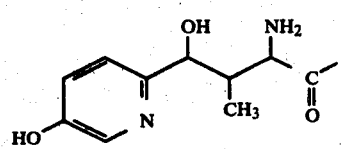

Nikkomicins are valuable agents for combating plant pests, and they can be used, for example, as insecticides, or especially as acaricides or fungicides. In this respect, the following nikkomicins of the formulae (X) and (Z), and mixtures thereof, contained in the nikkomicin mixture obtained by microbiological preparation have proved to be particularly important:

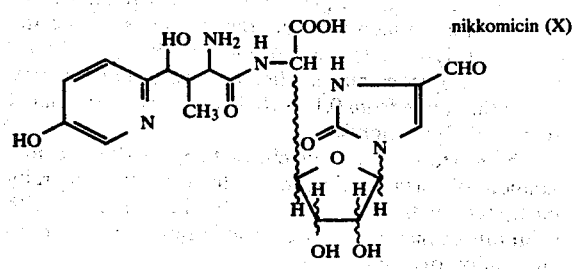

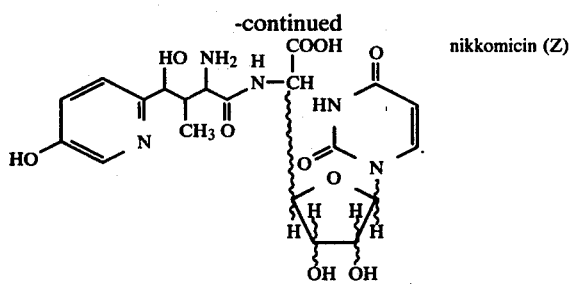

As already indicated, nikkomicins, in particular the nikkomicins of formulae (X) and (Z) and mixtures thereof, can be used for combating pests, preferably as fungicides and as insecticides, and in particular as acaricides. However, in certain use forms and under adverse moist conditions, for example weather conditions, the long-term action of the nikkomicins is not completely satisfactory in all cases.

The present invention now provides, as new compounds, heavy metal salts, preferably Cr, Fe, Co, Ni, Cu and Zn salts, of nikkomicins, in particular of the nikkomicins of formulae (X) and (Z), as defined above, and mixtures thereof.

Particularly preferred heavy metal salts of nikkomicin according to the present invention are the Zn and Cu salts, especially the Zn salts.

The new heavy metal salts of nikkomicin according to the present invention are pulverulent substances, solutions of which in aqueous 0.1N HCl have the same spectral properties as a solution of "free" nikkomicin in 0.1N HCl, for example $UV_{\lambda max}$ (0.1N HCl): 230(sh)nm and 286 nm.

This method can be used for identifying the new substances.

According to the present invention there is further provided a process for the production of the new heavy metal salts of nikkomicin of the present invention characterized in that one or more nikkomicins, preferably nikkomicin of formula (X) or nikkomicin of formula (Z), as defined above, or a mixture thereof, is reacted with a water-soluble heavy metal salt in an aqueous medium.

The heavy metal salts employed in the process according to the invention are preferably water-soluble Cr, Fe, Co, Ni, Cu and Zn salts, particularly preferably Cu and Zn salts and especially Zn salts. Water-soluble heavy metal salts in which the heavy metals are in the divalent or trivalent form are preferably used. Heavy metal chlorides, sulphates and acetates, in particular sulphates, are preferred.

Examples which may be mentioned of heavy metal salts which can be used according to the invention are: $ZnCl_2$, $ZnSO_4 \times 7\ H_2O$, $Zn(CH_3COO)_2$, $CuCl_2 \times 2\ H_2O$, $CuSO_4 \times 5\ H_2O$, $Cu(CH_3COO)_2$, $Cu(NO_3)_2 \times 3\ H_2O$, $Cr_2(SO_4)_3 \times 18\ H_2O$, $Fe\ SO_4$, $Fe_2(SO_4)_3$, $FeCl_3$, $FeCl_2$, $CoCl_2$, $CoSO_4 \times 7\ H_2O$, $NiSO_4 \times 7\ H_2O$ and $NiCl_2 \times 6\ H_2O$. $CuSO_4$ and $ZnSO_4$ are particularly preferred.

The type and nature of the nikkomicin to be employed in the process according to the invention are essentially not critical.

The nikkomicin can be in a pure form or in the form of a crude nikkomicin which has already been prepurified by known processes and/or by the processes described below. It is also possible for the crude nikkomicin solution which has not been prepurified and which is obtained as a culture broth in the microbial production of nikkomicin to be employed, if necessary after concentration.

The weight ratios used for the starting substances in the process according to the invention are essentially not critical, and can easily be determined in accordance with the nature and form of the starting materials and the equipment available.

In general, 1 to 10, preferably 1 to 2, moles of heavy metal salt are employed per mole of nikkomicin. The molar data for nikkomicin relates to the pure nikkomicin (above all nikkomicin of formula (X) and the nikkomicin of formula (Z) which is contained in the crude product employed and has been determined by known methods with the aid of high pressure liquid chromatography (HPLC).

It is expedient for the heavy metal salt, if appropriate in aqueous solution, to be added in portions to an aqueous solution of nikkomicin (preferably 1 kg of crude nikkomicin in 2 to 20, in particular 2 to 4, liters of water), the pH value being kept at values between 6.0 and 7.5, preferably between 6.5 and 7.0, during the reaction by adding a base. An inorganic water-soluble base, such as NaOH or KOH, is preferably used as the base here. A 0.1-10 N solution of the heavy metal salt (preferably a 1-2 N solution) is added until no further precipitate is formed. The amount of heavy metal salt required can in this way be determined very simply.

It is expedient, in order to improve the yield, for an excess of heavy metal salt to be added and for the reaction mixture to be left to stand to after-react for some hours, until no further additional precipitate is formed. The reaction is preferably carried out at a temperature between 0° and 50° C., in particular between 15° and 25° C.

The heavy metal salt of nikkomicin which has precipitated is separated off by customary methods (filtration, centrifugation) and if appropriate washed with water and/or an organic solvent (for example acetone) and then dried.

As already mentioned above, purified or crude nikkomicin can be used as the starting material for the process according to the invention. Thus, for example, the product obtained according to German Offenlegungsschrift (German Published Specification) No. 2,537,028 and U.S. Pat. Nos. 4,046,881 and 4,158,608 can be employed.

A nikkomicin which has a high content of nikkomicin of formula (X) and nikkomicin of formula (Z) and which can particularly advantageously be employed for the process according to the invention can be obtained, for example, by treating crude nikkomicin or a culture broth containing nikkomicin with a basic ion exchanger, eluting the mixture of nikkomicins of formulae (X) and (Z) with an acid and isolating the resulting produce by customary methods.

Preferably, in this process, the culture filtrate obtained after the fermentation is treated with an acid ion exchanger in a first step. Crude nikkomicin solution which is particularly suitable for concentrating the nikkomicins of formulae (X) and (Z) is obtained on subsequent elution with ammonia.

A suitable crude nikkomicin solution can also be obtained in a particularly advantageous manner as follows:

If the crude nikkomicin is not already in the form of a solution or if a culture filtrate is employed, the crude nikkomicin is dissolved in, preferably, demineralized or distilled water. The concentration of the solution is not critical and is only restricted by the solubility of the nikkomicin on the one hand and the desire for an amount of liquid which can easily be handled (defined by the size of the equipment used) on the other hand. If the solution of the crude nikkomicin does not already have an appropriate pH value, it is brought to a pH value from 4 to 7, preferably from 6 to 7, by adding acid. All the customary inorganic acids (for example HCl) and, preferably, organic acids, in particular lower aliphatic carboxylic acids, such as acetic acid or propionic acid, which do not attack nikkomicin can be used here. Acetic acid is preferred.

The aqueous solution (which can also contain organic solvents, such as methanol) is brought into contact with the basic ion exchanger in the customary manner (for example by discharging onto a column or by stirring into a kettle). The most favorable amount of ion exchanger depends on the solution employed and on the nature of the ion exchanger and can easily be determined by customary methods.

All the customary basic ion exchangers can be used for this method for the preparation of the "crude nikkomicin". Examples which may be mentioned are: basic macroporous or gelatinous polystyrene resins which are crosslinked with divinylbenzene and which are partly or completely substituted by primary, secondary, tertiary or quaternary nitrogen groups. Macroporous and gelatinous ion exchangers which are derived from crosslinked polyacrylamide can also be used.

Furthermore, it is possible to use basic gelatinous or macroporous ion exchangers based on acrylates or methacrylates which have been transamidated with, for example, dimethylaminopropylamine. The functional nitrogen can be present in a primary, secondary, tertiary or quaternary grouping or as a mixture of these groupings. A macroporous amino-methylated polystyrene which is cross-linked with about 6% of divinylbenzene (see German Patent Specification No. 2,418,976 and U.S. Pat. No. 3,989,650) is particularly preferred as the weakly basic ion exchanger.

Gelatinous ion exchangers based on dextran can also be employed as basic ion exchangers.

Specific examples of basic ion exchangers which may be mentioned are: "Lewatit" MP 500 (Trade Mark of BAYER AG, Leverkusen, Germany (FRG), "Dowex" MSA-1 (Trade Mark of Dow Chemicals, USA) and DEAE-"Sephadex" A-25 and QAE-"Sephadex" A 25 (Trade Marks of Pharmacia, Uppsala, Sweden).

Preferably, the loaded ion exchanger is then washed once or several times with water.

Suitable solutions for eluting the pair of nikkomicins of formulae (X) and (Z) from the basic ion exchanger are dilute solutions of lower aliphatic carboxylic acids (for example acetic acid) which can easily be removed in a simple manner (for example by evaporation or by being entrained with other suitable solvents) without thereby changing the pH value in the direction of an acid medium to such an extent that hydrolysis, in particular hydrolysis of the pair of nikkomicins of formulae (X) and (Z), takes place. The concentration is preferably in the range from 0.1 to 10%, and is, in particular, 1 to 5% (% by weight).

The mixture of nikkomicin of formula (X) and nikkomicin of formula (Z) can be eluted by the generally customary methods, for example by simple stirring with solutions of increasing acid concentration or by gradient elution over a column.

When the basic ion exchanger loaded with the mixture of nikkomicin of formula (X) and nikkomicin of formula (Z) is stirred with solutions of increasing acid concentration, nikkomicin of formula (Z) is preferentially concentrated in the first fractions, while mainly nikkomicin of formula (X) is concentrated later at higher acid concentrations.

The ratio of nikkomicin of formula (X) to nikkomicin of formula (Z) in the mixture can thus be greatly influenced as desired, by separating off the particular relevant fractions.

The mixture of the nikkomicins of formulae (X) and (Z) is isolated from the eluate by the methods generally customary in biochemistry, for example by evaporating off the solvent, preferably under reduced pressure, or by freeze-drying.

As has already been mentioned above, a culture filtrate from the microbial production can also be used directly as the starting material for working up the nikkomicin, or it is also possible to use a concentrated crude nikkomicin solution, the concentrated solution being obtained by treating a culture filtrate with an acid ion exchanger in a preliminary stage, with subsequent elution with a weak base. This step is illustrated in more detail below.

The culture filtrate obtained in a known manner in the microbial production of nikkomicin is adjusted to a pH value of 2 to 5, preferably 3.5 to 4.5 and in particular 4, by adding an acid. Suitable acids in this context are those acids which are capable of establishing the above pH values. Lower aliphatic carboxylic acids, in particular acetic acid, are preferably used.

This solution is treated with an acid ion exchanger by generally customary methods.

The nikkomicins of formulae (X) and (Z) can be bonded, for example, by simply stirring the solution with the ion exchanger or by discharging the solution or allowing the nikkomicin solution to flow through a column packed with ion exchanger.

Suitable acid ion exchangers are, preferably, the customary macroporous or gelatinous ion exchangers of polystyrene resins which are crosslinked with divinylbenzene and have sulphonic acid groupings, for example "Lewatit" SC 104 (Trade Mark of BAYER AG, Leverkusen, Germany (FRG) and "Dowex" 50 WX 4 (Trade Mark of Dow Chemicals USA).

The loaded ion exchanger is preferably washed once or several times with water.

Weak bases, for example dilute ammonia, are suitable for eluting the pair of nikkomicins of formulae (X) and (Z) from acid ion exchangers. The concentration of the bases is preferably in the range from 0.01N to 0.1N, and is, in particular, 0.04 to 0.6N.

The elute or a solution of the crude nikkomicin isolated from the eluate is brought to the required pH value and treated with the basic ion exchanger, as described above.

All the nikkomicins obtained by these routes are outstandingly suitable starting substances for the process according to the invention.

Surprisingly, the new heavy metal salts of nikkomicin according to the invention have a superior long-term action compared with the "free" nikkomicins, especially in a moist environment, for example in rainy weather. The new compounds thus represent a valuable enrichment in the field of pest-combating agents.

The invention also relates to the use of the new active compounds for combating pests, preferably harmful fungi and Arthropodae, such as insects and Arachnidae. The new active compounds can particularly preferably be employed as acaricides.

The invention likewise relates to pest-combating agents which contain the new active compounds and to the preparation and use of these agents.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride aliphatic or alicyclic-hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for examle iron oxide, titanium oxide and Prussion Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in their commercially available formulations and in the use forms, prepared from these formulations, as a mixture with other active compounds, such as insecticides, baits, sterlizing agents, acaricides, nematicides, fungicides, growth-regulating substances or herbicides. The insecticides include, for example, phosphates, carbamates, carboxylates, chlorinated hydrocarbons, phenylureas and substances produced by microorganisms.

The active compounds according to the invention can furthermore be present in their commercially available formulations and in the use forms, prepared from these formulations, as a mixture with synergistic agents. Synergestic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against pests harmful to health and pests of stored products, the active compounds are distinguished by an excellent residual action on wood and clay as well as by a good stability to alkali on limed substrates.

The present invention also provides pesticidal composition containing as active ingredient a compound of the present invention in admixture with a solid or liquefied gaseous diluent or carrier or in admixture with a liquid diluent or carrier containing a surface-active agent.

The present invention also provides a method of combating pests (in particular fungi and arthropods, especially insects or acarids) which comprises applying to the pests or to a habitat thereof, a compound of the present invention alone or in the form of a composition containing as active ingredient a compound of the present invention in admixture with a diluent or carrier.

The present invention further provides crops protected from damage by pests by being grown in areas in which immediately prior to and/or during the time of the growing a compound of the present invention was applied alone or in admixture with a diluent or carrier.

It will be seen that the usual methods of providing a harvested crop may be improved by the present invention.

The active compounds are well tolerated by plants and have a favorable level of toxicity to warm-blooded animals, and are suitable for combating fungi and Arthropodae, such as insects and Arachnidae, in particular spider mites, which are encountered in agriculture, in forests, in the protection of stored products and of materials, and in the hygiene sector. They are active against normally sensitive and resistant species and against all or some stages of development. The abovementioned pests include:

From the order of the Arachnida, for example, *Scorpio maurus* and *Latrodectus mactans*.

From the order of the Acarina, for example, *Acarus siro*, Argas, spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chroioptes spp., Sacroptes spp., Tarsonemus spp., *Bryobia praetoiosa*, Panonychus spp. and Tetranychus spp.

The active compounds according to the invention also exhibit a good fungicidal action, especially against rust diseases on various crop plants, such as species of Puccinia, species of Uromyces, *Phragmidium mucronatum*, species of Botrytis, above all *Botrytis cinerea* in vines, strawberries and vegetable crops, against species of Sclerotinia, against powdery mildew fungi, such as Erysiphe, and against species of Sphaerotheca. Furthermore, the active compounds according to the invention can also be employed against species of Venturia, species of Alternaria, *Pellicularia sasakii, Pyricularia oryzae* and species of Cercospora. In addition to treatment of the above-ground parts of plants, pathogens which attack the plants from the soil or are transmitted by the seed can also be combated with the active compounds according to the invention.

The preparation of the nikkomicin salts according to the invention may be illustrated with the aid of the following preparative examples in which all the % data denote percentages by weight:

PREPARATIVE EXAMPLES

Example 1

(a) Stepwise elution in the batch process 1 kg of crude nikkomicin (about 15% of nikkomicins of formulae (X) and (Z) was dissolved in 4 liters of demineralized $H_2O$ and the pH value of the solution was adjusted to 6.5 to 7.0 by adding acetic acid. This solution was added to 10 kg of a weakly basic ion exchanger (washed and adjusted to pH 7.0 with acetic acid) suspended in 16 liters of demineralized water, the pH value of the solution being kept at 6.5 to 7.0 by adding acetic acid, and the mixture was stirred for 1 hour. It was then filtered and the loaded exchanger resin was stirred with three 10 liter portions of water for in each case 15 minutes. The washed ion exchanger resin was then extracted stepwise by stirring with in each case 10 liters of acetic acid of increasing concentration (1%, 2%, 3%, 4%, 5% and 10%), in each case for ½ an hour, the pH value being kept constant during the particular extraction stage by adding acetic acid. A mixture containing up to 70% of the nikkomicins (X) and (Z) was obtained with a yield of 80%. The nikkomicin content was in each case determined by high pressure liquid chromatography (HPLC) by customary methods.

(b) 500 g of nikkomicin mixture (content of nikkomicins of formulae (X) and (Z)=55%) were dissolved in 2 liters of water and the resulting aqueous solution was adjusted to pH 6.5 to 7.0 with sodium hydroxide solution. 250 ml of 2N $ZnSO_4$ solution were then slowly added, the pH value of the solution being kept between 6.5 and 7.0 with sodium hydroxide solution.

The reaction mixture was cooled and the precipitate was filtered off. The precipitate was then washed with water, water/acetone and finally with acetone.

Precipitation again from the mother liquor with 100 ml of 2N $ZnSO_4$ solution gave a further small amount of precipitate, which was treated analogously.

310 g of the Zn salt of nikkomicin with a content of nikkomicin (X) and nikkomicin (Z) of 85.6% (HPLC) and with a zinc content of 8.3% were obtained. The yield was 96.5%, relative to the nikkomicin employed.
Decomposition point: 255° C.

Example 2

5 kg of crude nikkomicin (15 to 30%) were dissolved in 20 liters of demineralized water and the pH value was adjusted to 6.5 to 7.0 with acetic acid. 80 liters of demineralized water and 50 kg of a weakly basic ion exchanger (washed and adjusted to pH 7.0 with acetic acid) were initially introduced into a receiver with a stirrer. The crude nikkomicin solution was added and the mixture was stirred for 60 minutes. The pH value was kept at 6.5 to 7.0 by adding the appropriate amount of acetic acid. The loaded ion exchanger was washed twice with 100 liters of demineralized water each time. The ion exchanger was then introduced into a conical glass column. The column was eluted with a linear gradient, obtained from 600 liters of demineralized water and 600 liters of 10% strength acetic acid. The first runnings from the column were discarded. Elution of the nikkomicin was followed with the aid of the pH value and the conductivity.

The degree of purity was about 90%, with a yield of 70 to 80%.

(b) 200 ml of 1N $ZnSO_4$ solution were added to 10 liters of nikkomicin eluate (containing 62.6 g of nikkomicin) and the pH value of the solution was kept between 6.5 and 7.0 with sodium hydroxide solution.

Working up was carried out as in Example 1.

72 g of the Zn salt of nikkomicin were obtained.

Example 3

10 g of a nikkomicin mixture (content of nikkomicins of formulae (X) and (Z) according to HPLC=50%) were dissolved in 50 ml of $H_2O$ and the resulting aqueous solution was adjusted to pH 6.5 to 7.0 with sodium hydroxide solution.

14 ml of 1N $CuSO_4$ solution were slowly added thereto, the pH value of the solution being kept between 6.5 and 7.0 with NaOH solution. The mixture was cooled and filtered. The precipitate was then washed with water, water/acetone and finally with acetone. 7.3 g of the Cu salt of nikkomicin with a content of nikkomicin of formula (X) and nikkomicin of formula (Z) of 62% (according to HPLC) were obtained. The yield was 90%, relative to the nikkomicin of formula (X) and nikkomicin of formula (Z) employed.

Suitable formulations of the nikkomicin salts of the present invention are illustrated with the aid of the following examples. The formulations are obtained by thorough mixing of the constituents listed. All the % data relate to percentages by weight.

Example 4

25.0% of the Zn salt of nikkomicin (according to Example 1)
1.5% of Na alkylarylsulphonate
8.0% of condensed Na alkylarylsulphonate
35.0% of adipic acid
10.0% of zinc sulphate
remainder quartz flour

Example 5

25.0% of Cu salt of nikkomicin (according to Example 3)
10.0% of C 14 myristyl alcohol
10.0% of zinc sulphate
15.0% of adipic acid
8.0% of condensed Na alkylarylsulphonate
10.0% of synthetic silica
remainder quartz flour

Example 6

12.5% of Zn salt of nikkomicin (according to Example 2)
12.5% of Cu salt of nikkomicin (according to Example 3)
1.0% of Na alkylarylsulphonate
5.0% of condensed Na alkylarylsulphonate
10.0% of synthetic silica
remainder: quartz flour

Example 7

12.5% of Cu salt of nikkomicin (according to Example 3)
1.0% of Na alkylarylsulphonate
5.0% of condensed Na alkylarylsulphonate
10.00% of synthetic silica
remainder: quartz flour The surprising superiority of the new active compounds compared with the previously known "free" nikkomicin in a moist to wet medium is illustrated by the following biotest example:

Example 8

(a) Description of the method

Female tetranychus urticae were allowed to lay eggs on a leaf of a bean plant in an area surrounded by banding grease, and the females were removed again. The leaves thus prepared were immersed in the aqueous suspensions of the nikkomicin salts, formulated as active compound preparations or wettable powder formulations of nikkomycin salts, in the appropriate concentration. One day after the treatment, spraying with distilled water in an amount corresponding to 12.5 mm of rain was carried out.

After the experimental period had ended, the surviving spider mites of all stages were counted and related to the starting population consisting only of eggs. The destruction in % was obtained.

(b) Experimental results

| Active compound | % by weight of active compound (based on nikkomicin) | % destruction after 12 days |
| --- | --- | --- |
| Experiment (i) | | |
| Zn salt of nikkomicin, active compound preparation (Example 6) | 0.02 | 100 |
| Nikkomicin | 0.02 | 16 |
| Experiment (ii) | | |
| Cu salt of nikkomicin; active compound preparation (Example 7) | 0.02 | 100 |
| Nikkomicin | 0.02 | 44 |

It will be appreciated that the instant specification and examples are set forth by way of illustration and not limitation and that various modifications and changes may be made without departing from the spirit and scope of the present invention.

What is claimed is:

1. A heavy metal salt of nikkomicin (X) of the formula

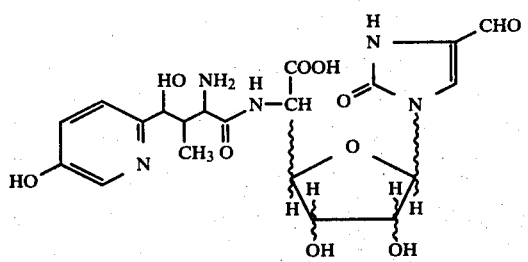

or nikkomicin (Z) of the formula

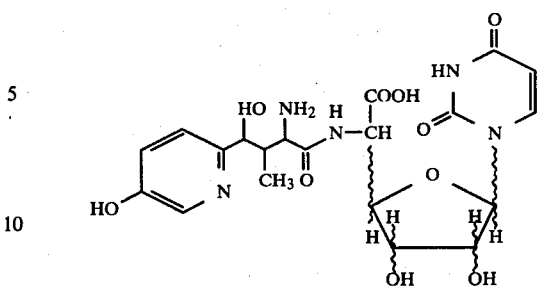

wherein the heavy metal salt is selected from the group consisting of Cr, Fe, Co, Ni, Cu and Zn.

2. A compound according to claim 1, which is a Cu salt or Zn salt of nikkomicin.

3. An arthropodicidal and fungicidal composition comprising an arthropodicidally and fungicidally effective amount of a compound according to claim 1 in admixture with a diluent.

4. A method of combating arthropods and fungi which comprises applying to the arthropods or fungi, or to a habitat thereof, an arthropodicidally or fungicidally effective amount of a compound according to claim 1.

5. A method of combating arthropods and fungi which comprises applying to the arthropods or fungi, or to a habitat thereof, an arthropodicidally or fungicidally effective amount of a compound according to claim 2.

* * * * *